(12) United States Patent
Kondo (10) Patent No.: US 12,364,809 B2
(45) Date of Patent: Jul. 22, 2025

(54) DRUG SOLUTION ADMINISTRATION APPARATUS AND DRUG SOLUTION ADMINISTRATION SET

(71) Applicant: TERUMO KABUSHIKI KAISHA, Tokyo (JP)

(72) Inventor: Akira Kondo, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 959 days.

(21) Appl. No.: 17/487,378

(22) Filed: Sep. 28, 2021

(65) Prior Publication Data

US 2022/0008651 A1 Jan. 13, 2022

Related U.S. Application Data

(63) Continuation of application No. PCT/JP2020/006081, filed on Feb. 17, 2020.

(30) Foreign Application Priority Data

Mar. 29, 2019 (JP) .................................. 2019-065710

(51) Int. Cl.
*A61M 5/145* (2006.01)
*A61M 5/158* (2006.01)
*A61M 5/172* (2006.01)

(52) U.S. Cl.
CPC .......... *A61M 5/1452* (2013.01); *A61M 5/158* (2013.01); *A61M 5/172* (2013.01); *A61M 2205/70* (2013.01)

(58) Field of Classification Search
CPC .... A61M 5/1452; A61M 5/158; A61M 5/172; A61M 2205/70; A61M 2005/14208; A61M 5/14248; A61M 2205/10; A61M 2205/50
See application file for complete search history.

(56) References Cited

U.S. PATENT DOCUMENTS 4,560,979 A 12/1985 Rosskopf
2008/0294094 A1* 11/2008 Mhatre ............. A61M 5/14248
604/65

(Continued)

FOREIGN PATENT DOCUMENTS

JP S59207161 A 11/1984
JP S59228851 A 12/1984
(Continued)

OTHER PUBLICATIONS

The extended European Search Report issued Mar. 17, 2022, by the European Patent Office in corresponding European Patent Application No. 20783598.4-1122. (9 pages).

(Continued)

*Primary Examiner* — Theodore J Stigell
(74) *Attorney, Agent, or Firm* — Buchanan Ingersoll & Rooney PC (57) ABSTRACT

A drug solution administration apparatus and a drug solution administration set in which the control unit can accurately detect completion of administration of a drug solution on the basis of the state of contact between the plunger and the switch. Before a drug solution administration apparatus is in use, a plunger included in the drug solution administration apparatus is disposed in a housing in the state where the plunger is non-contact with a switch, and a control unit is configured to, prior to start of administration of a drug solution, conduct an operation test of checking whether the switch is turned on when the plunger is moved forward by a predetermined distance and, after it is confirmed that the switch is turned on in the operation test, to perform an administration start operation for administering the drug solution.

16 Claims, 7 Drawing Sheets

(56) References Cited

U.S. PATENT DOCUMENTS

| | | | |
|---|---|---|---|
| 2012/0215170 A1* | 8/2012 | Traversaz | A61M 5/14546 |
| | | | 604/154 |
| 2014/0296787 A1 | 10/2014 | Agard et al. | |
| 2017/0151388 A1 | 6/2017 | Monrad et al. | |
| 2020/0001004 A1 | 1/2020 | Kondo | |

FOREIGN PATENT DOCUMENTS

| | | |
|---|---|---|
| JP | H09294807 A | 11/1997 |
| JP | 2000350782 A | 12/2000 |
| JP | 2017519597 A | 7/2017 |
| WO | 2018168988 A1 | 9/2018 |

OTHER PUBLICATIONS

International Search Report (PCT/ISA/210) with translation and Written Opinion (PCT/ISA/237) mailed on Apr. 14, 2020, by the Japanese Patent Office as the International Searching Authority for International Application No. PCT/JP2020/006081. (8 pages).

* cited by examiner

DRUG SOLUTION ADMINISTRATION APPARATUS AND DRUG SOLUTION ADMINISTRATION SET

CROSS-REFERENCES TO RELATED APPLICATIONS

This application is a continuation of International Application No. PCT/JP2020/006081 filed on Feb. 17, 2020, which claims priority to Japanese Patent Application No. 2019-065710 filed on Mar. 29, 2019, the entire content of both of which is incorporated herein by reference.

FIELD OF THE DISCLOSURE

The present disclosure generally relates to a drug solution administration apparatus and a drug solution administration set.

BACKGROUND DISCUSSION

Syringe pump type drug solution administration apparatuses for administering a drug solution filled in a drug solution container to a living body by a pressing action provided by a plunger are known. A drug solution administration apparatus of this type includes a tubular drug solution container, a plunger that pushes out the drug solution contained in the drug solution container, and a gasket (see, for example, JP H9-294807 A).

For checking the state of administration of a drug solution filled in the drug solution container, the control unit provided in the drug solution administration apparatus is configured to make a determination. When the plunger moves forward toward the distal end of the drug solution container by a predetermined distance, the control unit checks the state of the switch that is turned on when the switch comes into contact with the plunger. When the switch comes into contact with the plunger and is turned on, the control unit detects that administration of the drug solution has started. When the switch becomes out of contact with the plunger and is turned off, the control unit detects that administration of the drug solution has completed.

In accordance with an aspect, a drug solution administration apparatus for administering a drug solution is disclosed, the drug solution administration apparatus comprising: a drug solution container configured to be filled with the drug solution; a gasket configured to be slidable on an inner wall of the drug solution container and to push out the drug solution contained in the drug solution container; a plunger configured to press the gasket, the plunger including a recess extending along an axial direction of the plunger; a drive mechanism configured to move the plunger toward a distal end of the drug solution container; and a switch configured to be turned on when in contact with the plunger and to be turned off when not in contact with the plunger.

In accordance with another aspect, a method for a drug solution from a drug solution administration apparatus, the method comprising: filling a drug solution container with the drug solution, the drug solution container including an opening through which the drug solution is discharged on a distal end of the drug solution container; moving the plunger toward the distal end of the drug solution container with a drive mechanism and causing a plunger to press into a gasket and sliding the gasket on an inner wall of drug solution container to push out the drug solution contained in the drug solution container; turning on a switch when in contact with the plunger and turning off the switch when not in contact with the plunger; wherein before the drug solution administration apparatus is in use, disposing the plunger in a state where the plunger is not in contact with the switch; and prior to start of administration of the drug solution, conducting an operation test of checking whether the switch is turned on when the plunger is moved by a predetermined distance with the control unit, and, after confirming that the switch is turned on in the operation test, performing an administration start operation for administering the drug solution.

The drug solution administration apparatus may be stored over a predetermined period of time before being used for administering a drug solution. If the plunger and the switch are constantly in contact with each other during such storage, the recovering force of the switch can decrease. When the recovering force of the switch decreases, the switch can fail to be turned off even in a state where the load of the plunger is no longer imposed on the switch. As a result, in spite of the fact that the drug solution has been completely administered and the plunger and the switch become out of contact, there is a possibility that the control unit erroneously recognizes that administration of the drug solution is not completed yet and makes an error notification.

SUMMARY

A drug solution administration apparatus and a drug solution administration set are disclosed in which the control unit can accurately detect completion of administration of a drug solution on the basis of the state of contact between the plunger and the switch.

The drug solution administration apparatus of the present disclosure is a drug solution administration apparatus for administering a drug solution, the drug solution administration apparatus including: a drug solution container that is filled with the drug solution and includes an opening through which the drug solution is allowed to be discharged, the opening being formed at a distal end of the drug solution container; a gasket that is slidable on an inner wall of drug solution container and is to push out the drug solution contained in the drug solution container; a plunger that is capable of pressing the gasket; a housing that houses the drug solution container and the plunger; a drive mechanism that moves forward the plunger toward the distal end of the drug solution container; a switch that is turned on when being in contact with the plunger and is turned off when being non-contact with the plunger; and a control unit that controls an operation of the drive mechanism and checks a state of the switch, in which before the drug solution administration apparatus is in use, the plunger is disposed in the housing in a state where the plunger is non-contact with the switch, and the control unit is configured to, prior to start of administration of the drug solution, conduct an operation test of checking whether the switch is turned on when the plunger is moved forward by a predetermined distance and, after it is confirmed that the switch is turned on in the operation test, to perform an administration start operation for administering the drug solution.

The drug solution administration apparatus and the drug solution administration set according to the present disclosure enable the control unit to accurately detect completion of administration of a drug solution on the basis of the state of contact between the plunger and the switch.

DETAILED DESCRIPTION

Set forth below with reference to the accompanying drawings is a detailed description of embodiments of to a drug solution administration apparatus and a drug solution administration set. Note that since embodiments described below are preferred specific examples of the present disclosure, although various technically preferable limitations are given, the scope of the present disclosure is not limited to the embodiments unless otherwise specified in the following descriptions. In addition, dimensional ratios in the drawings are exaggerated for convenience of description and may be different from actual ratios.

Figure 1:
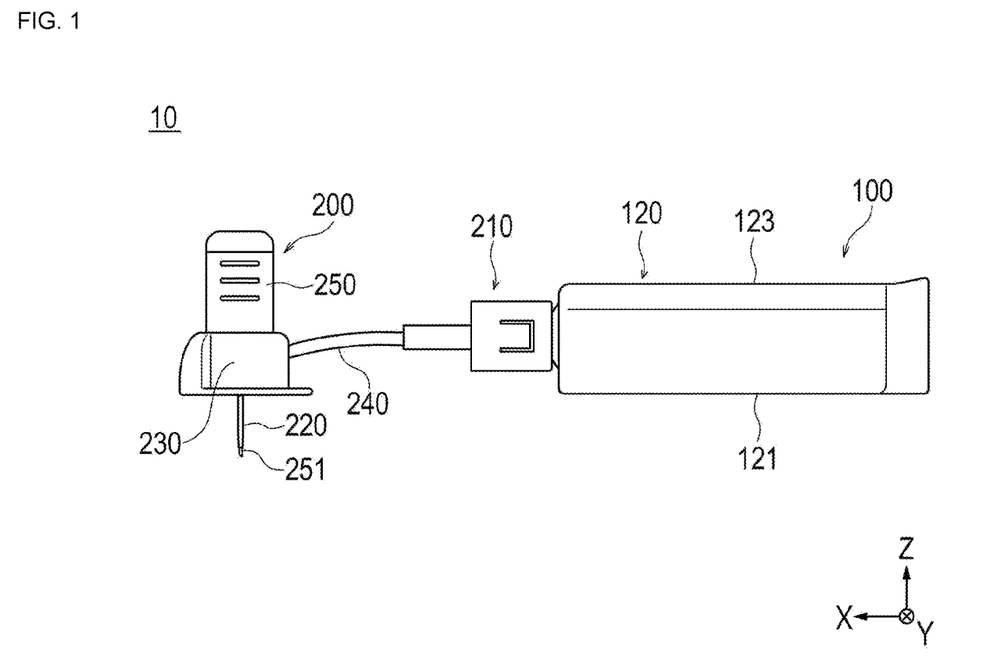
FIG. 1 is a side view of a drug solution administration set according to an embodiment of the present disclosure.
Figure 2:
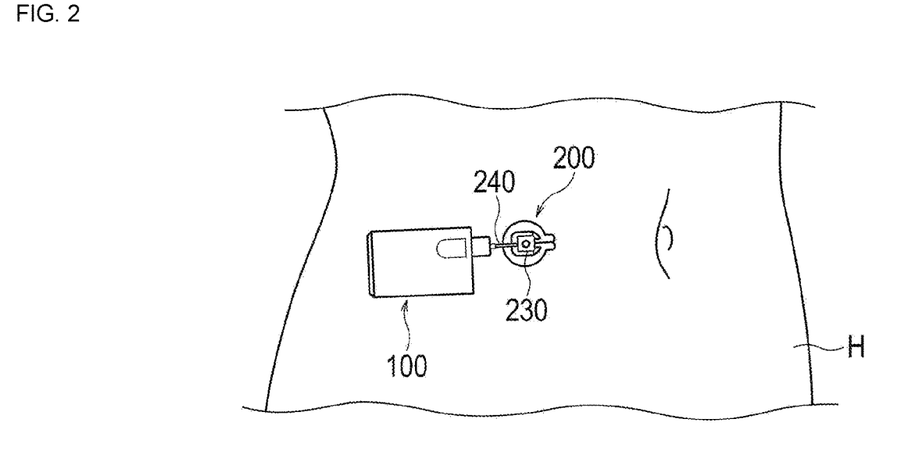
FIG. 2 is a diagram schematically illustrating a usage example of the drug solution administration set shown in FIG. 1.
Figure 3:
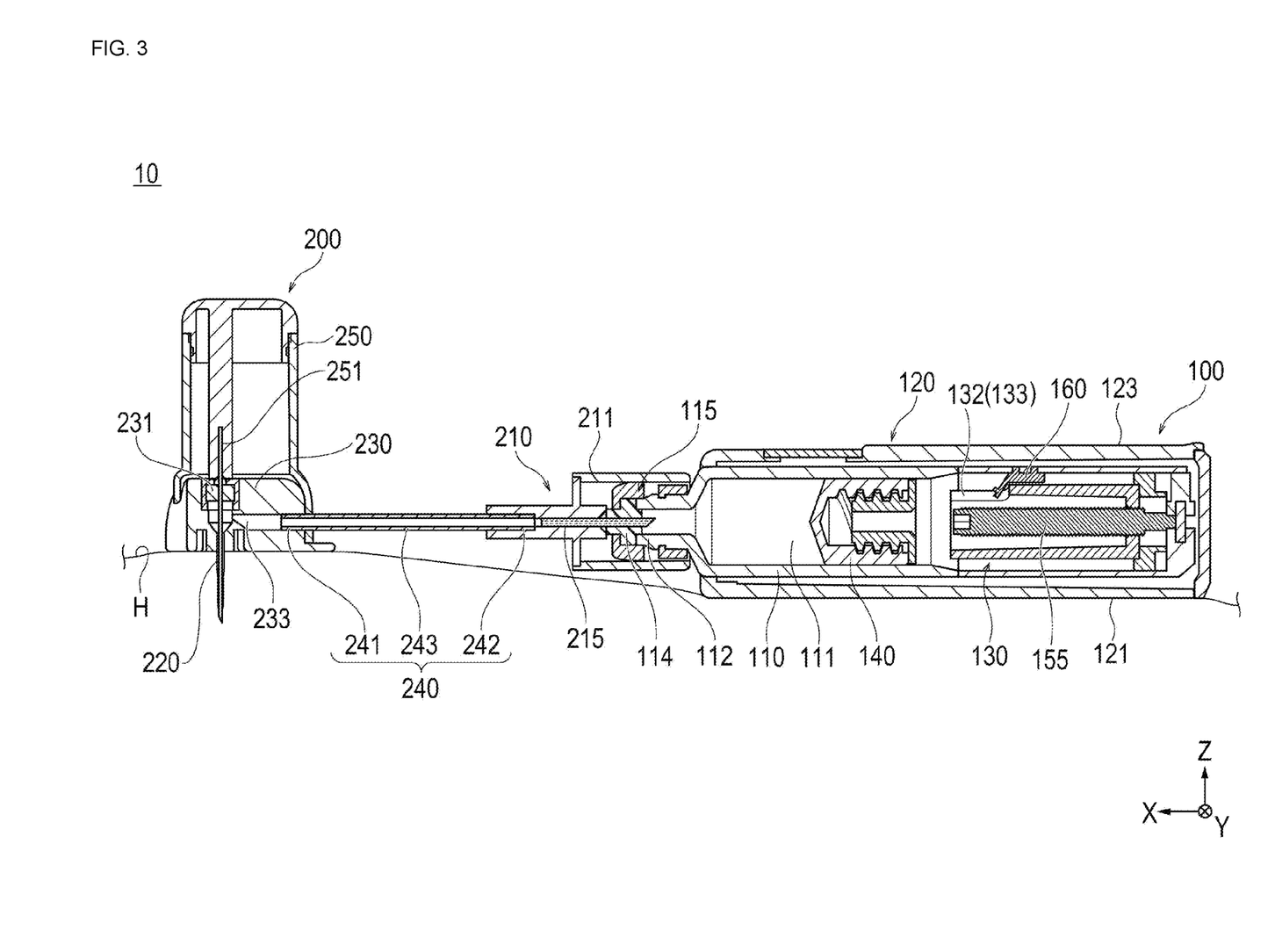
FIG. 3 is a cross-sectional view of the drug solution administration set shown in FIG. 1.

FIGS. 1 to 7 are diagrams for explaining a drug solution administration set 10, a drug solution administration apparatus 100, and an administration instrument 200 according to an embodiment of the present disclosure. In the drawings, an arrow X indicates the "longitudinal direction (axial direction of a plunger 130)" of the drug solution administration apparatus 100, an arrow Y indicates the "width direction (depth direction)" of the drug solution administration apparatus 100, and an arrow Z indicates the "height direction" of the drug solution administration apparatus 100. The cross-sectional view shown in FIG. 3 is a vertical cross-sectional view (an X-Z cross sectional view) of the drug solution administration apparatus 100 and the administration instrument 200.

Drug Solution Administration Set

The drug solution administration set 10 can be used for administering a drug solution into a living body. As illustrated in FIG. 1, the drug solution administration set 10 includes the drug solution administration apparatus 100 and the administration instrument 200 connectable to the drug solution administration apparatus 100.

As illustrated in FIGS. 2 and 3, when the drug solution administration set 10 is used to administer a drug solution, the drug solution administration apparatus 100 and a needle hub unit 230 in the administration instrument 200 are attached to a body surface (e.g., skin) H of the user. The site of the user body to which the drug solution administration apparatus 100 and the needle hub unit 230 are attached is not particularly limited, and examples of the site of the user body can include the abdomen and thighs.

The drug solution administration set 10 is capable of continuously administering a drug solution filled in a drug solution container 110 included in the drug solution administration apparatus 100 into a living body over a relatively long period of time (for example, about several minutes to several hours) by a pressing action provided by the plunger 130 and a gasket 140. The drug solution administration set 10 may intermittently administer a drug solution into a living body.

Drug Solution Administration Apparatus

Figure 5:
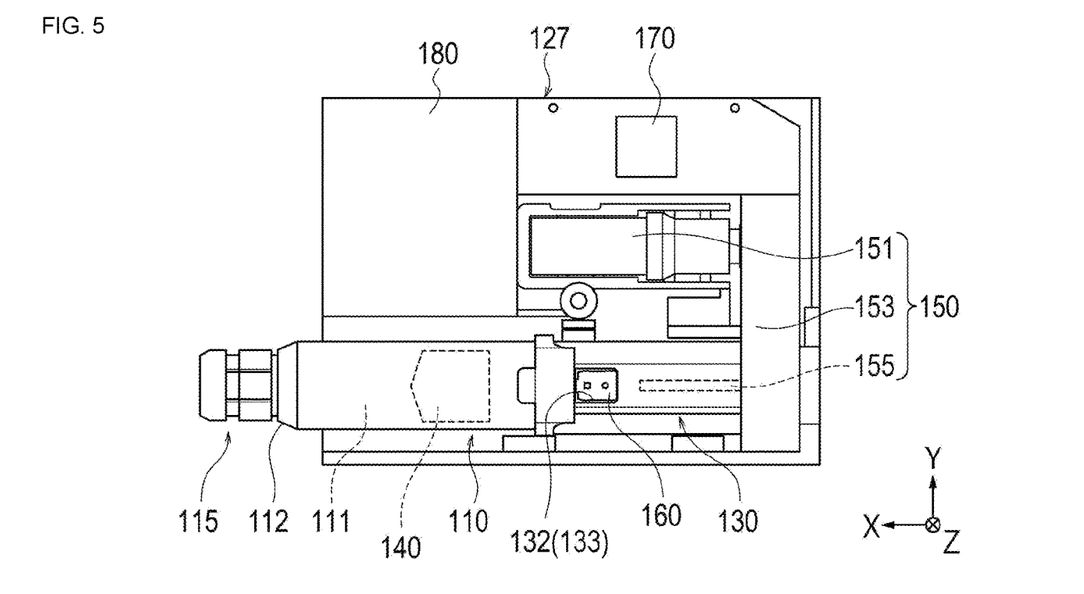
FIG. 5 is a plan view schematically illustrating the inside of a housing of the drug solution administration apparatus.

As illustrated in FIGS. 3 and 5, the drug solution administration apparatus 100 includes: a drug solution container 110 that is filled with a drug solution and includes an opening through which the drug solution can be discharged, the opening being formed at a distal end 112; a gasket 140 that is slidable on an inner wall of the drug solution container 110 and is to push out the drug solution contained in the drug solution container 110; a plunger 130 that is capable of pressing the gasket 140; a housing 120 that houses the drug solution container 110 and the plunger 130; a drive mechanism 150 that moves forward the plunger 130 toward the distal end of the drug solution container 110; a switch 160 that is turned on when being in contact with the plunger 130 and is turned off when being in non-contact with the plunger 130; and a control unit 170 that controls operations of the drive mechanism 150 and checks the state of the switch 160. The distal end of the drug solution container 110 protrudes from the housing 120.

In accordance with an exemplary embodiment, the housing 120 can be formed of a box-shaped member having a housing space formed in the box-shaped member. A chassis 127 illustrated in FIG. 5 is housed inside the housing 120.

Figure 4:
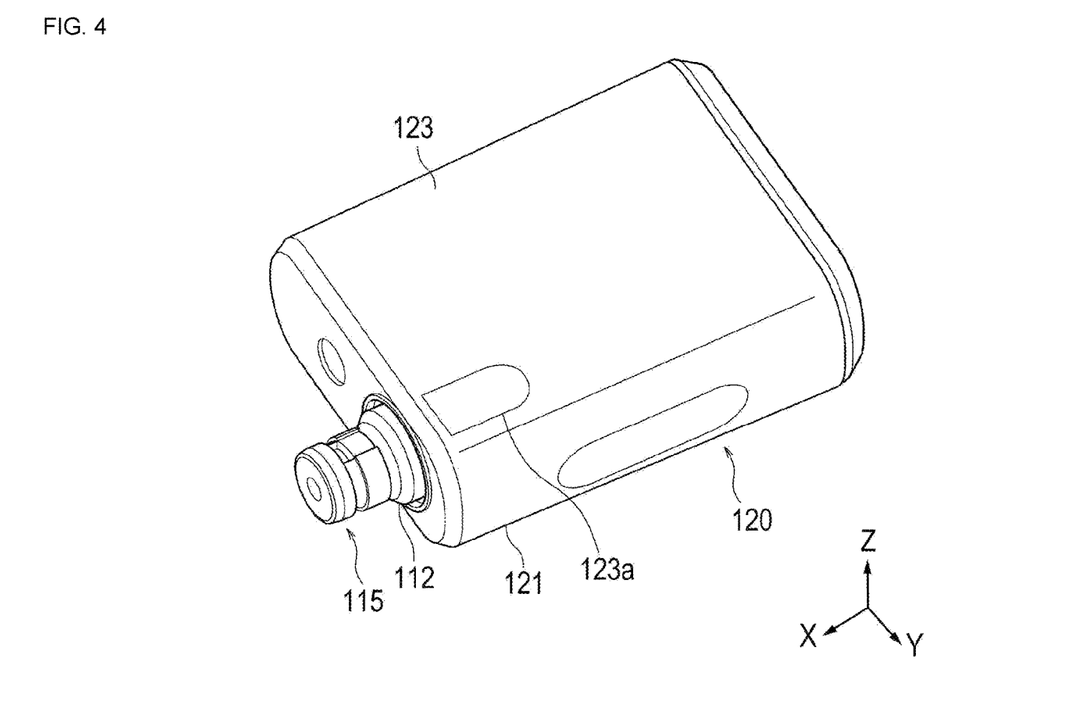
FIG. 4 is a schematic perspective view of a drug solution administration apparatus.

As illustrated in FIG. 4, a window part 123a is formed on a top surface 123 of the housing 120 so that the inside of the housing 120 can be visually recognized or seen from the outside of the housing 120. The window part 123a can be formed by providing a transparent or translucent portion in a part of the housing 120.

On a bottom surface 121 of the housing, a sheet-like sticking part that can be stuck on the body surface H of the user can be provided. In an initial state before the drug solution administration apparatus 100 is attached to the user, a peelable protective sheet is attached to the sticking surface of the sticking part.

As illustrated in FIG. 5, the drug solution container 110, the plunger 130, the gasket 140, the drive mechanism 150, the control unit 170, and the power supply unit 180 are disposed in the chassis 127.

In accordance with an exemplary embodiment, the drug solution container 110 can be formed of a tubular body including an inner cavity 111 that is to be filled with a drug solution. The gasket 140 is disposed in the inner cavity 111 of the drug solution container 110. The gasket 140 can be made of, for example, a rubber material or a resin material such as an elastomer. The gasket 140 liquid-tightly seals the proximal end side of the gasket 140 by bringing the outer periphery of the gasket 140 into close contact with the inner peripheral surface of the drug solution container 110 in a liquid-tight manner.

The drug solution container 110 is formed of a so-called prefilled type drug solution container. Therefore, the drug solution is filled in advance in the inner cavity 111 of the drug solution container 110. Examples of the drug solution can include protein preparations, narcotic analgesics, and diuretics.

The plunger 130 is configured to be movable forward, as caused by the drive mechanism 150, with respect to the drug solution container 110 toward the distal end side (lower side in FIG. 3) of the drug solution container 110. The plunger 130 moves the gasket 140 disposed in the drug solution container 110 toward the distal end 112 of the drug solution container 110, thereby pushing the drug solution from the inner cavity 111 of the drug solution container 110 toward the needle tube 220.

Figure 10:
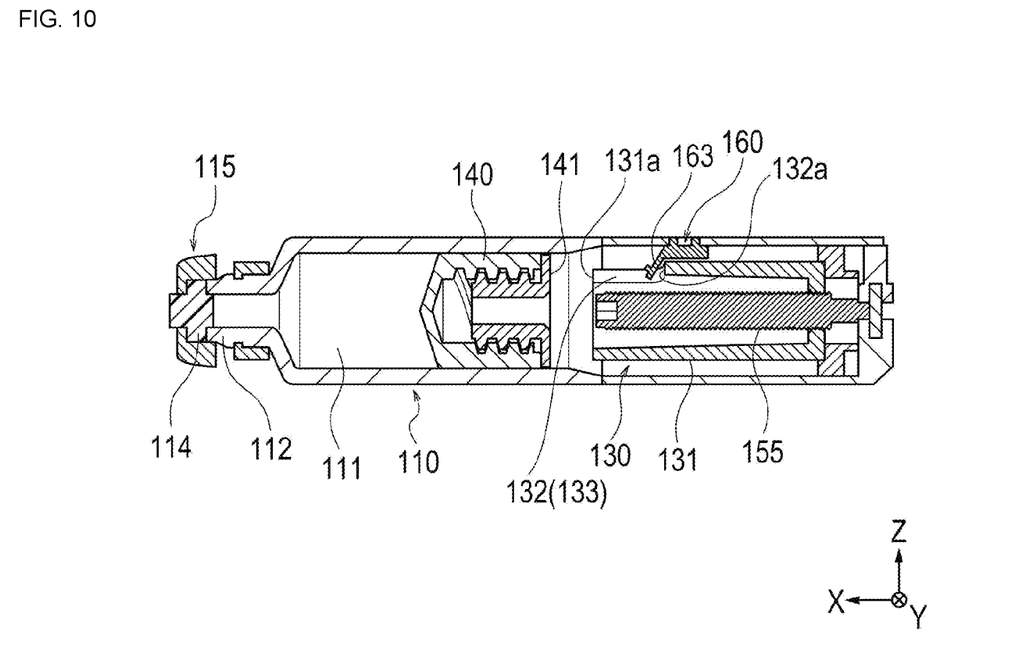
FIG. 10 is a cross-sectional view for explaining an operation example of the drug solution administration apparatus.
Figure 11:
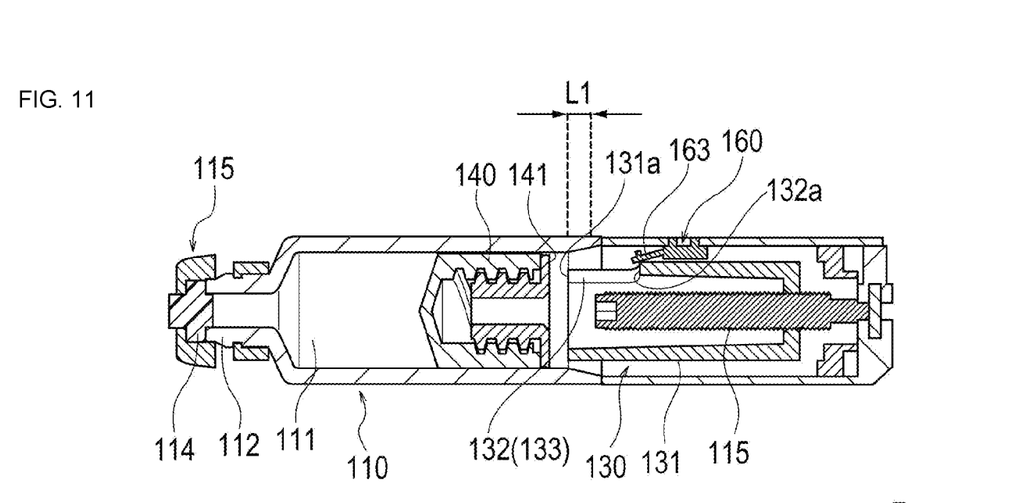
FIG. 11 is a cross-sectional view for explaining an operation example of the drug solution administration apparatus.

As illustrated in FIGS. 10 and 11, the plunger 130 can be separated from the gasket 140 by a distance greater than a predetermined distance L1 before the drug solution administration apparatus 100 is in use so that there is still a gap between the plunger 130 and the gasket 140 after the plunger 130 moves forward by the predetermined distance L1 in an operation test.

In the present embodiment, the gasket 140 is configured to be contractible in a direction (axial direction of the plunger 130) in which the plunger 130 moves forward when the plunger 130 moves forward in a state where the gasket 140 is pressed against the distal end inner wall of the drug solution container 110. The gasket 140 can be made of, for example, a rubber material or a flexible resin material such as an elastomer.

As illustrated in FIG. 3, a seal member 114 that helps prevent leakage of a drug solution is disposed at the opening (discharge port) of the drug solution container 110. The opening of the drug solution container 110 is disposed so as to protrude outward from the housing 120. On the drug solution container 110, an attachment 115 to be connected to a connector 210 (see FIG. 1) is attached to the distal end protruding from the housing 120.

Figure 8:
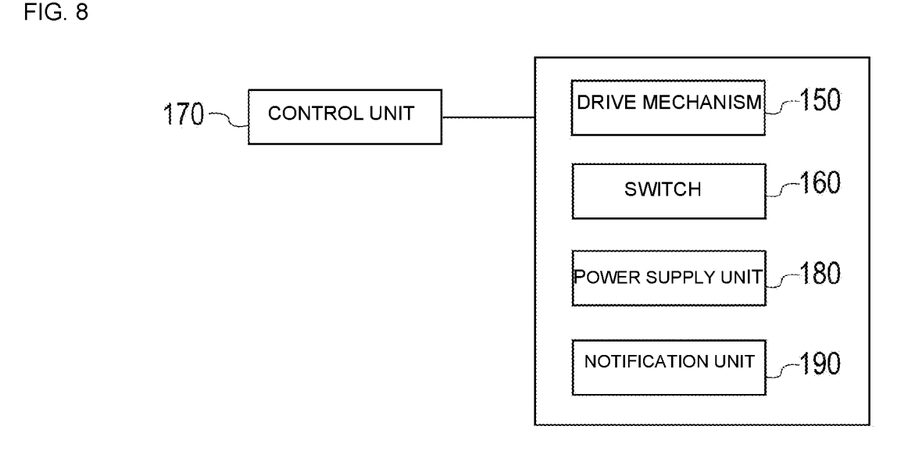
FIG. 8 is a block diagram schematically showing a control system of the drug solution administration apparatus.

FIG. 8 schematically illustrates a control system of the control unit 170. The control unit 170 controls operations of the drive mechanism 150, the switch 160, the power supply unit 180, and a notification unit 190 in a centralized manner (i.e., all-inclusively). The control unit 170 can be, for example, a known microcomputer (electronic circuit element) in which a central processing unit (CPU), a random-access memory (RAM), a read-only memory (ROM), and the like are mounted.

Figure 6:
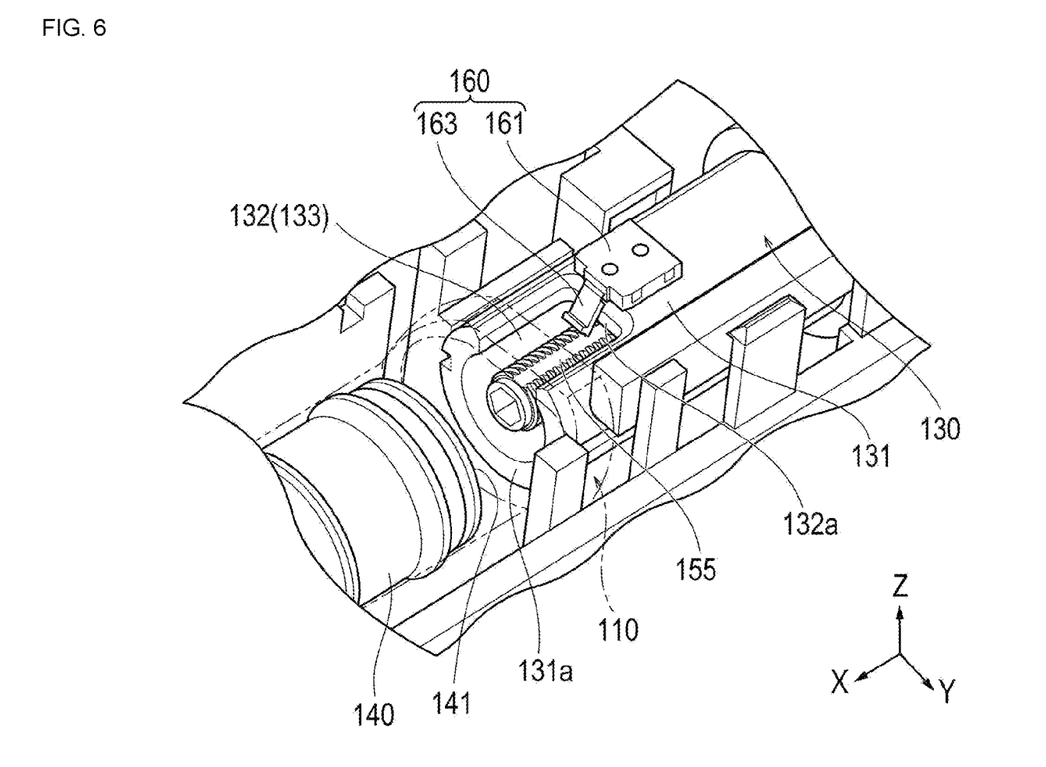
FIG. 6 is a perspective view showing a plunger recess and a switch.

As illustrated in FIGS. 3 and 6, the switch 160 can be disposed on the inner side of the top surface 123 of the housing 120. The switch 160 can include a connection part 161 connected to the housing 120 and a detection end 163. The switch 160 is turned on when the plunger 130 comes into contact with the detection end 163. The switch 160 is turned off when the detection end 163 and the plunger 130 become out of contact with each other.

The switch 160 can be formed of, for example, a known contact-type sensor that transmits a predetermined electric signal when the plunger 130 comes into contact with the detection end 163. The control unit 170 is capable of detecting whether the switch 160 is on or off on the basis of presence or absence of a received electric signal transmitted by the switch 160. Note that the switch 160 is not particularly limited to any specific configuration (for example, shape, structure, arrangement, and the like) as long as the switch can be turned on or off depending on the contact or non-contact state with the plunger 130.

The power supply unit 180 can be, for example, a battery or the like.

In accordance with an exemplary embodiment, the notification unit 190 notifies the user that delivery of the drug solution has been completed. The notification unit 190 can be, for example, a speaker or the like that produces voices or sounds. The notification unit 190 can be disposed at any position in the housing 120.

As illustrated in FIG. 5, the drive mechanism 150 can include a motor 151 that receives a drive current from the power supply unit 180 to generate a rotational driving force, a deceleration mechanism 153 including, for example, gears for transmitting the rotational driving force of the motor 151, and a feed screw 155 connected to the deceleration mechanism 153.

The feed screw 155 converts a rotary motion transmitted from the deceleration mechanism 153 into a linear motion to move forward the plunger 130 in the axial direction (X direction).

Figure 7:
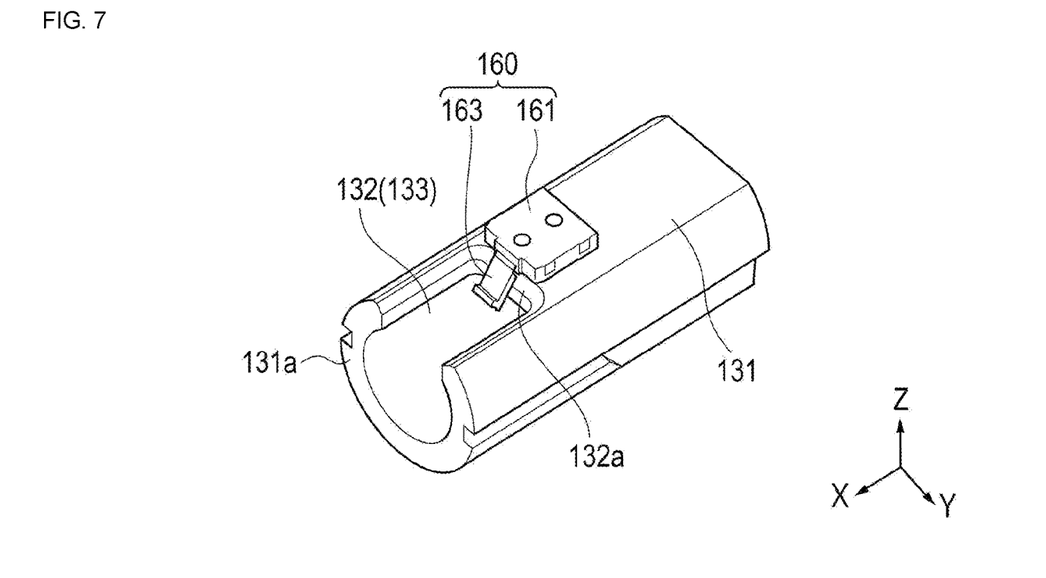
FIG. 7 is a perspective view showing the plunger.

As illustrated in FIGS. 6 and 7, the plunger 130 can include a tubular body 131 and a recess 132 extending along the axial direction of the plunger 130.

The recess 132 can be provided as a slit 133 obtained by cutting a distal end of the plunger 130. The recess 132 extends to the distal end opening of the tubular body 131. No particular limitation is imposed on the shape of the recess 132 (slit 133), the specific position of the recess 132 (slit 133) formed in the tubular body 131, and the like.

Before the drug solution administration apparatus 100 is in use, the plunger 130 is disposed in the housing 120 in the state where the plunger 130 is in non-contact with the detection end 163 of the switch 160. As illustrated in FIG. 6, the switch 160 is disposed on the proximal end side of the drug solution container 110 and near the proximal end of the drug solution container 110, and is placed in the recess 132, thereby maintaining the state where the switch 160 is in non-contact with the tubular body 131. When the plunger 130 moves forward by a predetermined distance L1, the switch 160 comes into contact with the proximal end 132a of the recess 132 (i.e., plunger 130) and is turned on (See FIGS. 11 and 12).

Figure 12:
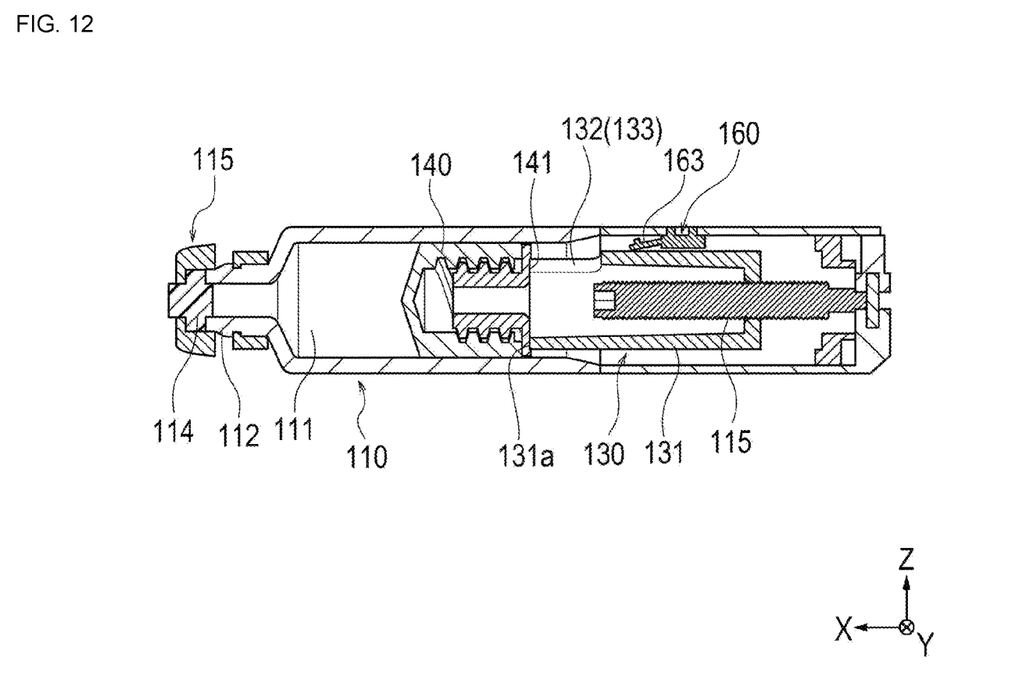
FIG. 12 is a cross-sectional view for explaining an operation example of the drug solution administration apparatus.
Figure 13:
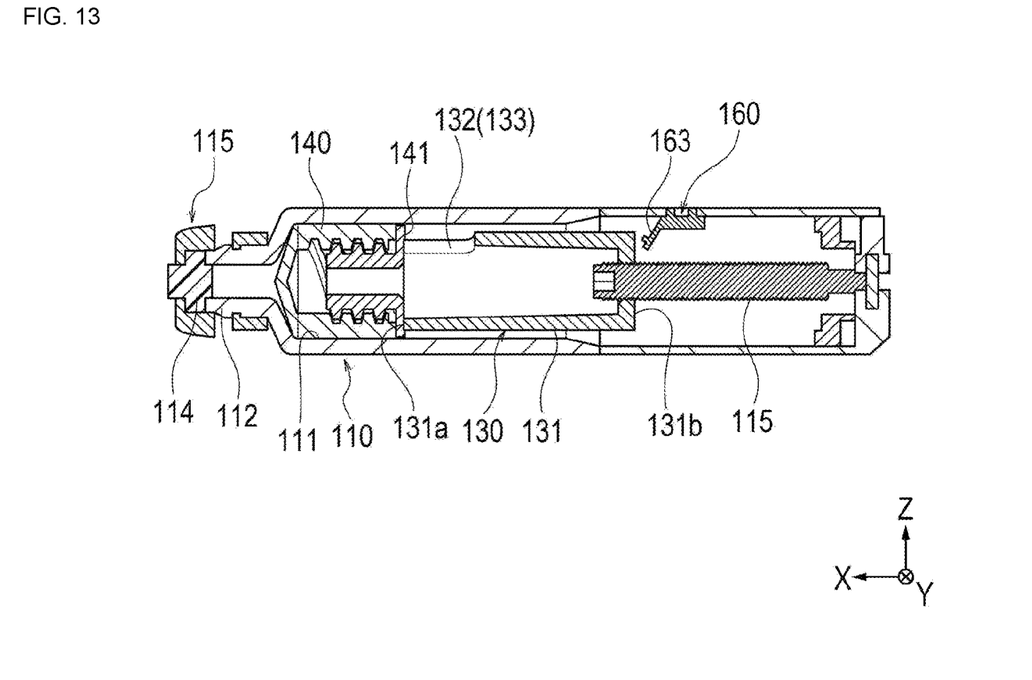
FIG. 13 is a cross-sectional view for explaining an operation example of the drug solution administration apparatus.

As illustrated in FIG. 12, the plunger 130 maintains contact with the switch 160 while the drug solution is administered. As illustrated in FIG. 13, the plunger 130 becomes out of contact with the switch 160 when, or immediately before, the administration of the drug solution is completed.

A method of controlling the drug solution administration apparatus 100 according to the present embodiment will be described.

Figure 9:
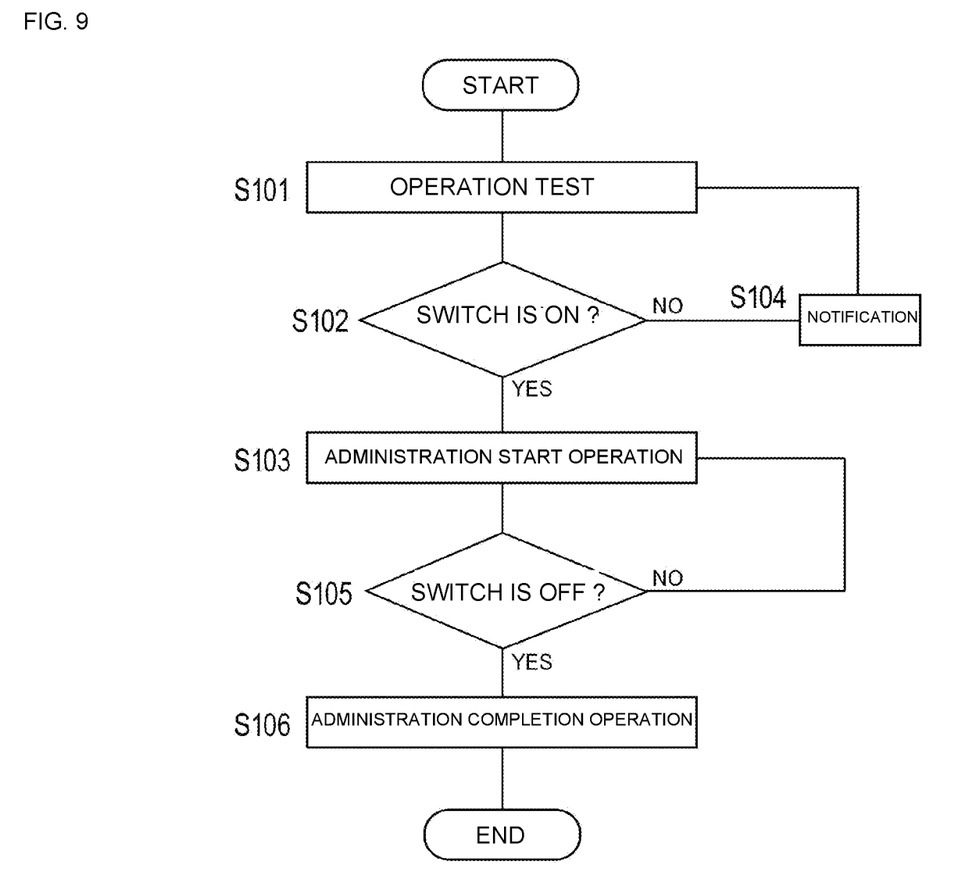
FIG. 9 is a flowchart showing a method of controlling the drug solution administration apparatus.

As shown in FIG. 9, the method of controlling the drug solution administration apparatus 100 includes an operation test (S101), checking whether the switch is on (S102), an administration start operation (S103), a notification operation (S104), checking whether the switch is off (S105), and an administration completion operation (106).

In the present embodiment, before the drug solution administration apparatus 100 starts administering a drug solution, the control unit 170 conducts an operation test of checking whether the switch 160 is turned on when the plunger 130 is moved forward by a predetermined distance L1 (see FIGS. 10 and 11). After confirming that the switch 160 is turned on in the operation test, the control unit 170 performs the administration start operation for administering the drug solution.

The following specifically describes the control method performed by the control unit 170 with reference to FIGS. 9 to 13.

As illustrated in FIG. 10, before administration of a drug solution is started, the switch 160 and the plunger 130 are disposed to be in non-contact with each other. In addition, a gap can be provided between the proximal end 141 of the gasket 140 and the distal end 131a of the plunger 130.

Before administration of a drug solution is started, the control unit 170 conducts an operation test (S101). As illustrated in FIG. 11, the control unit 170 moves forward the plunger 130 by a predetermined distance L1.

In accordance with an exemplary embodiment, the control unit 170 may perform, prior to the operation test, a priming operation of filling the needle tube 220 and the solution delivery tube 240 (see FIG. 3) with the drug solution before the living body of the user is punctured with the needle tube 220 of the administration instrument 200. The "administration start operation" described in the present embodiment means an operation for starting administration of a drug solution into the body of the user. Therefore, the priming operation is not included in the administration start operation.

When the plunger 130 is moved forward by a predetermined distance L1, the control unit 170 checks the state of the switch 160 (S102). If it is confirmed that the switch 160 is turned on (S102: YES), the control unit 170 performs the administration start operation for administering a drug solution (S103). Note that the control unit 170 may start the administration start operation when a certain time period has passed after detecting that the switch 160 is turned on. Thus, the control unit 170 may not necessarily start administering the drug solution immediately after the switch 160 is turned on.

If it is not confirmed that the switch 160 is turned on when the plunger 130 is moved forward by a predetermined distance L1 (S102: NO), the control unit 170 determines that a malfunction has occurred in the switch 160 and makes notification of an error (S104). After making notification of an error, the control unit 170 proceeds with the operation test. Note that the control unit 170 may stop the operation test after making notification of an error.

As illustrated in FIG. 12, the plunger 130 moves forward the gasket 140 disposed on the distal end side of the plunger 130 toward the distal end 112 of the drug solution container 110, thereby delivering the drug solution to the administration instrument 200 (see FIG. 3). The plunger 130 maintains contact with the switch 160 while the drug solution is administered.

If it is confirmed that the switch 160 is turned off (S105: YES), the control unit 170 performs the completion operation of administration of the drug solution, triggered by turning-off of the switch 160 (S106). As illustrated in FIG. 13, the proximal end 131b of the plunger 130 comes to the distal end side beyond the detection end 163 of the switch 160, whereby the plunger 130 and the switch 160 become out of contact with each other, and the switch 160 is turned off.

Note that the plunger 130 and the switch 160 may become out of contact with each other upon completion of administration of the drug solution or immediately before completion of administration of the drug solution. For example, in cases where installation, dimensions, or the like of the individual components such as the drug solution container 110, the plunger 130, and the switch 160 is less accurate, the switch 160 may fail to be turned off even when the gasket 140 has moved forward until its distal end is pressed against an inner wall of the distal end of the drug solution container 110. The control unit 170 continues to move forward the plunger 130 unless the switch 160 is turned off. Therefore, the administration operation by the drug solution administration apparatus 100 is not stopped. As in the present embodiment, if the plunger 130 and the switch 160 are configured to become out of contact with each other immediately before completion of administration of a drug solution, the plunger 130 and the switch 160 are enabled to become out of contact with each other more reliably when the plunger 130 is moved forward by a predetermined distance even in cases where installation, dimensions, or the like of the individual components is less accurate.

If it is not confirmed that the switch 160 is turned off during the administration operation (S105: NO), the control unit 170 continues the administration operation.

Administration Instrument

The following describes the administration instrument 200.

As illustrated in FIGS. 1 and 3, the administration instrument 200 includes a connector 210, a needle hub unit 230, a solution delivery tube 240, and a puncture aid 250.

As illustrated in FIG. 3, the connector 210 includes a connector body 211 connectable to the attachment 115 attached to the drug solution container 110 and a communication part 215 communicable with the inner cavity 111 of the drug solution container 110. The communication part 215 of the connector 210 is formed of a hollow needle tube capable of passing through the seal member 114 disposed in the drug solution container 110.

As illustrated in FIG. 3, the needle hub unit 230 includes a needle holding part 231 that holds the needle tube 220 and a communication path 233 that communicates with the inner cavity of the needle tube 220.

As illustrated in FIG. 3, the solution delivery tube 240 includes a first end 241 connected to the needle hub unit 230, a second end 242 connected to the connector 210, and an intermediate portion 243 extending between the first end 241 and the second end 242.

The solution delivery tube 240 delivers the drug solution from the inner cavity 111 of the drug solution container 110 to the needle tube 220 via the communication part 215 of the connector 210 and the communication path 233 of the needle hub unit 230.

When the drug solution is going to be delivered to the user, the puncture aid 250 is attached to the needle hub unit 230. The puncture aid 250 holds an introducer needle (inner needle) 251. As illustrated in FIGS. 1 and 3, in a state where the puncture aid 250 is attached to the needle hub unit 230, the introducer needle 251 protrudes from the tip of the needle tube 220. By puncturing the living body with the needle tube 220 in a state where the introducer needle 251 is inserted through the needle tube 220, the user can insert the needle tube 220 into the living body while helping prevent breakage or the like of the needle tube 220.

After the living body is punctured with the needle tube 220, the puncture aid 250 is removed from the needle hub unit 230. When the puncture aid 250 is removed from the needle hub unit 230, the introducer needle 251 is removed from the inner cavity of the needle tube 220.

After the puncture aid 250 is removed from the needle hub unit 230, the needle tube 220 is left (i.e., remains) in the living body. The plunger 130 and the gasket 140 in the drug solution administration apparatus 100 move forward inside the drug solution container 110, whereby the drug solution filled in the drug solution container 110 is delivered to the inner cavity of the needle tube 220 via the solution delivery tube 240.

The introducer needle 251 can be formed of, for example, a metal needle. The needle tube 220 can be formed of, for example, a tubular member (cannula) made of resin.

As with the drug solution administration apparatus 100, the administration instrument 200 can be configured as a patch-type instrument to be attached to the body surface H of the user before use. On the bottom surface of the needle hub unit 230 of the administration instrument 200, a sheet-like sticking part that can be stuck on the body surface can be provided. In an initial state before the administration instrument 200 is attached to the user, a peelable protective sheet can be attached to the sticking surface of the sticking part provided on the bottom surface.

As described above, the drug solution administration apparatus 100 according to the present embodiment is a drug solution administration apparatus for administering a drug solution, the drug solution administration apparatus including: the drug solution container 110 that is filled with a drug solution and includes an opening through which the drug solution can be discharged, the opening being formed at a distal end of the drug solution container 110; the gasket 140 that is slidable on an inner wall of the drug solution container 110 and is to push out the drug solution contained in the drug solution container 110; the plunger 130 that is capable of pressing the gasket 140; the housing 120 that houses the drug solution container 110 and the plunger 130; the drive mechanism 150 that moves forward the plunger 130 toward the distal end 112 of the drug solution container 110; the switch 160 that is turned on when being in contact with the plunger and is turned off when being non-contact with the plunger 130; and the control unit 170 that controls operations of the drive mechanism 150 and checks the state of the switch 160, in which before the drug solution administration apparatus 100 is in use, the plunger 130 is disposed in the housing 120 in a state where the plunger 130 is non-contact with the switch 160, and the control unit 170 is configured to, prior to start of administration of a drug solution, conduct an operation test of checking whether the switch 160 is turned on when the plunger 130 is moved forward by a predetermined distance L1 and, after it is confirmed that the switch 160 is turned on in the operation test, to perform an administration start operation for administering the drug solution.

The drug solution administration apparatus 100 configured as above makes it possible to help prevent the occurrence of contact failure and the like due to a decrease in the recovering force of the switch 160 because the switch 160 and the plunger 130 are disposed in the state of non-contact with each other before the drug solution administration apparatus 100 is in use. The drug solution administration apparatus 100 is capable of effectively preventing a decrease in the recovering force of the switch 160 in a case where, for example, the drug solution container 110 is a prefilled-type drug solution container and is stored under refrigeration over a long period of time. In addition, the drug solution administration apparatus 100 is capable of detecting an operation failure of the switch 160 prior to an administration start operation for administering a drug solution because the drug solution administration apparatus 100 is configured to perform the administration start operation after confirming that the switch 160 is turned on in an operation test.

In accordance with an exemplary embodiment, the plunger 130 maintains contact with the switch 160 while the drug solution is administered, and becomes out of contact with the switch 160 when, or immediately before, the administration of the drug solution is completed. The control unit 170 performs the completion operation of administration of the drug solution, triggered by turning-off of the switch 160. Therefore, the drug solution administration apparatus 100 can perform the administration completion operation at an appropriate timing on the basis of the switching between the state where the switch 160 and the plunger 130 are in contact with each other and the state where the switch 160 and the plunger 130 are in non-contact with each other.

In addition, the plunger 130 includes the recess 132 extending along the axial direction of the plunger 130. Before the operation test is started, the switch 160 is disposed in the recess 132 and maintains the state of non-contact with the plunger 130, and when the plunger 130 moves forward by a predetermined distance L1, the switch 160 comes into contact with the proximal end 132a of the recess 132 and is turned on. The switch 160 is disposed in the recess 132, whereby the drug solution administration apparatus 100 can reliably prevent the plunger 130 and the switch 160 from coming into contact with each other before the drug solution administration apparatus 100 is in use.

The switch 160 is disposed on the proximal end side of the drug solution container 110 and near the proximal end of the drug solution container 110, and the recess 132 is provided as the slit 133 obtained by cutting a distal end of the plunger 130. Therefore, when the drug solution administration apparatus 100 is assembled, the switch 160 can be placed along the slit 133, whereby the plunger 130 and the switch 160 can be reliably prevented from coming into contact with each other during the assembly work.

The plunger 130 is separated from the gasket 140 by a distance greater than a predetermined distance L1 before the drug solution administration apparatus 100 is in use so that there is still a gap between the plunger 130 and the gasket 140 after the plunger 130 moves forward by the predetermined distance L1. Therefore, the gasket 140 is not pressed by the plunger 130 during the operation test, thereby preventing a drug solution from being administered mistakenly.

The drug solution administration set 10 includes the drug solution administration apparatus 100 and the administration instrument 200 connectable to the drug solution administration apparatus 100. The administration instrument 200 includes: the connector 210 that includes the communication part 215 communicable with the inner cavity 111 of the drug solution container 110 and is connectable to the drug solution administration apparatus 100; the needle tube 220 that is to puncture a living body; the needle hub unit 230 that includes the needle holding part 231 holding the needle tube 220 and the communication path 233 communicating with the inner cavity of the needle tube 220; and the solution delivery tube 240 that includes the first end 241 connected to the needle hub unit 230 and the second end 242 connected to the connector 210, and that is capable of delivering a drug solution from the inner cavity 111 of the drug solution container 110 to the needle tube 220 via the communication part 215 of the connector 210 and the communication path 233 of the needle hub unit 230.

The drug solution administration set 10 as configured above enables the control unit 170 to accurately detect completion of administration of a drug solution on the basis of the state of contact between the plunger 130 and the switch 160 in the drug solution administration apparatus 100, thereby making it possible to administer an appropriate amount of the drug solution into the living body of the user.

The detailed description above describes embodiments of a drug solution administration apparatus and a drug solution administration set. The invention is not limited, however, to the precise embodiments and variations described. Various changes, modifications and equivalents may occur to one skilled in the art without departing from the spirit and scope of the invention as defined in the accompanying claims. It is expressly intended that all such changes, modifications and equivalents which fall within the scope of the claims are embraced by the claims.

What is claimed is:

1. A drug solution administration apparatus for administering a drug solution, the drug solution administration apparatus comprising:
a drug solution container configured to be filled with the drug solution and includes an opening through which the drug solution is discharged, the opening being formed at a distal end of the drug solution container;
a gasket configured to be slidable on an inner wall of drug solution container and configured to push out the drug solution contained in the drug solution container;
a plunger configured to press the gasket, the plunger includes a recess extending along an axial direction of the plunger;
a housing that houses the drug solution container and the plunger;
a drive mechanism configured to move the plunger toward the distal end of the drug solution container;
a switch configured to be turned on when in contact with the plunger and to be turned off when not in contact with the plunger; and
a control unit configured to control an operation of the drive mechanism and to check a state of the switch, wherein
before the drug solution administration apparatus is in use, the plunger is disposed in the housing in a state where the plunger is not in contact with the switch,
the control unit is configured to, prior to start of administration of the drug solution, conduct an operation test of checking whether the switch is turned on when the plunger is moved by a predetermined distance and, after it is confirmed that the switch is turned on in the operation test, to perform an administration start operation for administering the drug solution; and
before the operation test is started, the switch is disposed in the recess and maintains a state of non-contact with the plunger, and when the plunger moves forward by the predetermined distance, the switch comes into contact with a proximal end of the recess and is turned on.

2. The drug solution administration apparatus according to claim 1, wherein
the plunger is configured to maintain contact with the switch while the drug solution is administered, and becomes out of contact with the switch when, or immediately before, administration of the drug solution is completed; and
the control unit is configured to perform a completion operation of administration of the drug solution, triggered by turning-off of the switch.

3. The drug solution administration apparatus according to claim 1, wherein
the switch is disposed on a proximal end side of the drug solution container and near a proximal end of the drug solution container; and
the recess is provided as a slit obtained by cutting a distal end of the plunger.

4. The drug solution administration apparatus according to claim 1, wherein the plunger is separated from the gasket by a distance greater than the predetermined distance before the drug solution administration apparatus is in use so that there is still a gap between the plunger and the gasket after the plunger moves forward by the predetermined distance.

5. The drug solution administration apparatus according to claim 1, further comprising:
the drug solution.

6. The drug solution administration apparatus according to claim 1, wherein the control unit is a microcomputer that includes at least a central processing unit.

7. The drug solution administration apparatus according to claim 1, further comprising:
a notification unit configured to notify a user that delivery of the drug solution has been completed.

8. A drug solution administration set comprising:
the drug solution administration apparatus according to claim 1; and
an administration instrument configured to be connected to the drug solution administration apparatus, wherein the administration instrument comprises:
a connector that includes a communication part communicable with an inner cavity of the drug solution container and is connectable to the drug solution administration apparatus;
a needle tube configured to puncture a living body;
a needle hub unit that includes a needle holding part holding the needle tube and a communication path communicating with an inner cavity of the needle tube; and
a tube that includes a first end connected to the needle hub unit and a second end connected to the connector, and is configured to deliver the drug solution from the inner cavity of the drug solution container to the needle tube via the communication part of the connector and the communication path of the needle hub unit.

9. A drug solution administration apparatus for administering a drug solution, the drug solution administration apparatus comprising:
a drug solution container configured to be filled with the drug solution;
a gasket configured to be slidable on an inner wall of the drug solution container and to push out the drug solution contained in the drug solution container;
a plunger configured to press the gasket, the plunger including a recess extending along an axial direction of the plunger;
a drive mechanism configured to move the plunger toward a distal end of the drug solution container;
a switch configured to be turned on when in contact with the plunger and to be turned off when not in contact with the plunger;
a control unit configured to control an operation of the drive mechanism and to check a state of the switch, wherein before the drug solution administration apparatus is in use, the plunger is disposed in a state where the plunger is not in contact with the switch;
the control unit is configured to, prior to start of administration of the drug solution, conduct an operation test of checking whether the switch is turned on when the plunger is moved by a predetermined distance and, after it is confirmed that the switch is turned on in the operation test, to perform an administration start operation for administering the drug solution; and
wherein before the operation test is started, the switch is disposed in the recess and maintains a state of non-contact with the plunger, and when the plunger moves forward by the predetermined distance, the switch comes into contact with a proximal end of the recess and is turned on.

10. The drug solution administration apparatus according to claim 9, wherein
the plunger is configured to maintain contact with the switch while the drug solution is administered, and becomes out of contact with the switch when, or immediately before, administration of the drug solution is completed; and
the control unit is configured to perform a completion operation of administration of the drug solution, triggered by a turning-off of the switch.

11. The drug solution administration apparatus according to claim 10, wherein the switch is disposed on a proximal end side of the drug solution container and near a proximal end of the drug solution container.

12. The drug solution administration apparatus according to claim 10, wherein the recess is a slit in a distal end of the plunger, and the plunger is separated from the gasket by a distance greater than the predetermined distance before the drug solution administration apparatus is in used so that there is still a gap between the plunger and the gasket after the plunger moves forward by the predetermined distance.

13. A method for administering the drug solution from the drug solution administration apparatus according to claim 1, the method comprising:
filling the drug solution container with the drug solution;
moving the plunger toward the distal end of the drug solution container with the drive mechanism and causing the plunger to press into the gasket and sliding the gasket on the inner wall of drug solution container to push out the drug solution contained in the drug solution container;
turning on the switch when in contact with the plunger and turning off the switch when not in contact with the plunger;
wherein before the drug solution administration apparatus is in use, disposing the plunger in the state where the plunger is not in contact with the switch;
prior to start of administration of the drug solution, conducting the operation test of checking whether the switch is turned on when the plunger is moved by the predetermined distance with the control unit, and, after confirming that the switch is turned on in the operation test, performing the administration start operation for administering the drug solution; and
before the operation test is started, disposing the switch in the recess and maintaining the state of non-contact with the plunger, and when the plunger moves forward by the predetermined distance, contacting the switch with the proximal end of the recess and turning on the switch.

14. The method according to claim 13, further comprising:
maintaining contact between the plunger and the switch while the drug solution is administered;
stopping the contact between the plunger and the switch when, or immediately before, administration of the drug solution is completed; and
triggering a completion operation of the administration of the drug solution by a turning-off of the switch.

15. The method according to claim 13, further comprising:
disposing the switch on a proximal end side of the drug solution container and near a proximal end of the drug solution container; and
providing the recess as a slit in a distal end of the plunger.

16. The method according to claim 13, further comprising:
separating the plunger from the gasket by a distance greater than the predetermined distance before the drug solution administration apparatus is in used so that there is still a gap between the plunger and the gasket after the plunger moves forward by the predetermined distance.

* * * * *